United States Patent [19]

Carse

[11] 4,219,620
[45] Aug. 26, 1980

[54] DENTINE PIN

[76] Inventor: Murray D. Carse, Queensway House, Hatfield, Hertfordshire AL10 0NR, England

[21] Appl. No.: 883,987

[22] Filed: Mar. 6, 1978

[30] Foreign Application Priority Data

Mar. 11, 1977 [GB] United Kingdom ............... 10502/77

[51] Int. Cl.² ............................................. A61C 5/04
[52] U.S. Cl. ................................................. 433/225
[58] Field of Search ...................... 32/15, 6, 7, 48, 27; 408/226

[56] References Cited

U.S. PATENT DOCUMENTS

| | | | |
|---|---|---|---|
| 2,338,437 | 1/1944 | Karlström ................................. | 32/27 |
| 3,098,299 | 7/1963 | Page ........................................ | 32/27 |
| 3,850,054 | 11/1974 | Weissman ................................ | 32/48 |

FOREIGN PATENT DOCUMENTS

| | | | |
|---|---|---|---|
| 2554179 | 10/1977 | Fed. Rep. of Germany .............. | 32/15 |
| 1253850 | 11/1968 | United Kingdom ....................... | 32/15 |
| 1347226 | 2/1974 | United Kingdom ....................... | 32/15 |
| 1347227 | 2/1974 | United Kingdom ....................... | 32/15 |

*Primary Examiner*—Louis G. Mancene
*Attorney, Agent, or Firm*—Blanchard, Flynn, Thiel, Boutell & Tanis

[57] ABSTRACT

A dentine pin has a screw-threaded portion intended to break off and remain in the dentine, a shank, and a latch portion for engagement by the latch of a dental handpiece. The shank is tapered or otherwise reduced in diameter to allow oscillation of the shank in the driving sleeve of the handpiece, thereby producing a self-aligning action.

4 Claims, 4 Drawing Figures

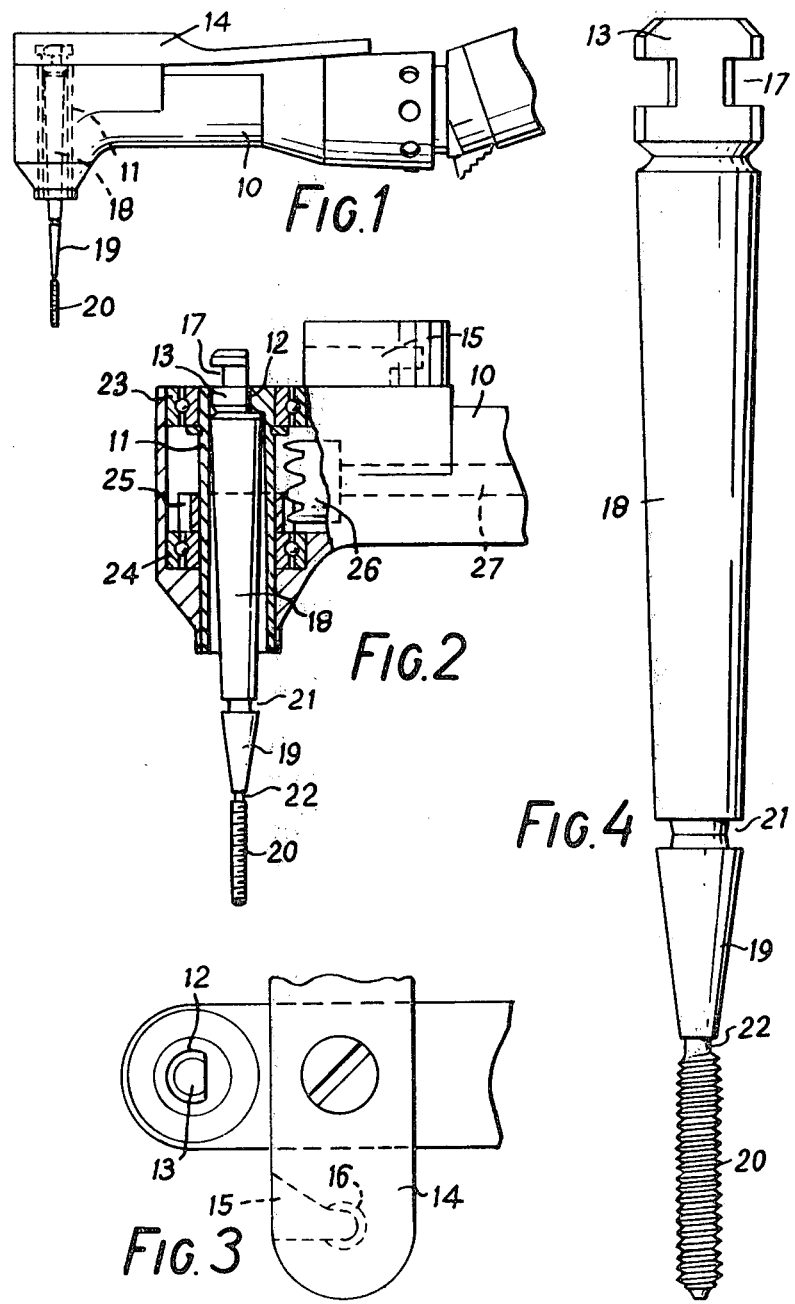

DENTINE PIN

The present invention relates to dentine pins which are used by dentists to attach fillings and restorations to teeth. The pins screw into drilled holes in the dentine of the tooth and project so that the filling or restoration can be formed round them.

A known form of dentine pin comprises a threaded portion which is attached by way of a neck to a cylindrical shank designed to fit into the handpiece of a dental drill. The shank has at its free end, remote from the threaded portion of the pin, a latching portion of non-circular section defined by forming a flat on the cylindrical shank and having a part-annular groove extending around the curved portion of its periphery. The cylindrical shank and latching portion are of conventional shape and dimensions in order to fit the standard type of dental handpiece which includes a cylindrical sleeve rotatable about its principal axis by the drive system of the drill, the sleeve having a non-circular opening at one end to effect driving engagement with the non-circular latching portion of the pin. The handpiece also has a latch which is engageable with the annular groove to hold the pin against axial movement while allowing it to be rotated by the sleeve.

This form of driving and latching mechanism is in general use for dental drills and burrs. When it is used with a dentine pin of the known form the threaded portion of the pin is engaged in a pre-drilled hole in the tooth and is screwed in by the hand-piece until it reaches the required depth, after which the threaded portion is broken off at the neck, leaving the shank in the hand-piece. Normally the resistance to further screwing in of the threaded portion is sufficient to cause it to shear off at the neck. The known dentine pin suffers from the disadvantage that it is difficult to align the pin with the pre-drilled hole in order to screw the pin into the dentine.

In accordance with the present invention a dentine pin for fitting in a standard dental handpiece, the pin comprising a shank with a latching portion at one end and a threaded portion attached to the other end of the shank by a neck is characterized in that the diameter of the shank decreases from a region adjacent the latching portion towards the neck in such a manner that the pin can oscillate within the sleeve of the handpiece, changing the inclination of the axis of the pin to the axis of the sleeve.

With such a form of pin the tip of the threaded portion describes a wandering path over a small area when the pin is rotated in the handpiece and this enables the tip to find the pre-drilled hole in the tooth without requiring the dentist to position the handpiece accurately. Furthermore the possibility of changing the angular position of the pin in the handpiece makes the pin self-aligning with respect to the pre-drilled hole.

The required reduction of the diameter of the shank can be achieved by tapering or stepping. The required taper may be quite small, for example with a semi-cone angle of no more than 3°.

A frusto-conical portion with a much larger angle of taper can be used to join the tapered shank to the neck of the pin. An annular groove can be formed at the junction between the shank and the frusto-conical portion to facilitate removal of the shank from the handpiece after the threaded portion has been broken off.

The threaded portion of the pin is preferably formed with a special thread form which has a sharp crest to the thread to enable it to cut into the dentine of the tooth to reduce the lateral compression of the dentine and give a secure fixing. The alloy steel used for the pin is so chosen and heat-treated that the threaded portion can be bent through an angle in excess of 90° with the thread performing a "concertina" action, i.e. expanding on the outside of the bend and being compressed to bring the turns closer to one another on the inside of the bend. Such bending may be necessary to shorten the threaded portion, to clear the opposing teeth, or to allow the threaded portions to fall within the contour of the final restoration.

The major feature is the floating action of the pin axis. This is produced by the reduction of the diameter of the shank that fits into the handpiece, which automatically compensates for mis-alignment of the handpiece in relation to the previously-drilled hole. When the pin is placed in the handpiece and it is rotated, the tip of the pin will describe a circle or some more complex figure. As soon as the tip is touched on to the tooth it will run true, but will have freedom to align itself, to the prepared pinhole. When the pin seats in the hole the neck will then give, and the threaded portion will separate.

The invention will now be described in more detail with the aid of an example illustrated in the accompanying drawings, in which:

FIG. 1 is a side view of part of a conventional dental handpiece fitted with a dentine pin in accordance with the invention, FIG. 2 is a detail on an enlarged scale with parts cut away, FIG. 3 is a top view showing the latch of the handpiece in the open position, and FIG. 4 is a side elevation of the dentine pin on a still larger scale.

The dental handpiece shown in the drawings is of entirely conventional form and includes an angled head piece 10 in which a drill, a burr, a dentine pin or other tool can be mounted. As shown particularly in FIG. 2 the shank of the tool fits into a cylindrical sleeve 11 of the handpiece.

The sleeve 11 is rotatable by the drive system of the handpiece and at its upper end, as best seen in FIG. 3, has an opening 12 of non-circular section which mates with a latching portion 13 of the tool (having a similar non-circular cross-section) to provide a driving connection to the tool. The non-circular section has the shape of a circle with a sector removed, leaving a straight side following a chord of the circle. The tool is held in place in the sleeve 11 by means of a releasable pivoted latch 14 on the handpiece (shown in the open position of FIG. 3) which has a notch 15 leading to a collar 16 which fits into a part-annular groove 17 on the latching portion of the tool to retain the tool against axial movement.

What has been described up to now of the handpiece and the manner of latching the tool into the handpiece is entirely conventional and standard practice. However, whereas known tools have cylindrical shanks to fit closely into the sleeve 11 the dentine pin shown in the drawings has a shank 18 which tapers from a large diameter adjacent the latching portion 13 to a small diameter near the other end of the sleeve 11. Alternatively a similar effect can be obtained by step-wise reduction of the diameter by one or more steps, each section from one step to the next being cylindrical. The rest of the pin comprises a frusto-conical portion 19 and a screw-threaded portion 20. An annular groove 21 is formed between the shank 18 and the portion 19 to facilitate removal of the shank from the handpiece. A shear-off neck 22 is formed between the portion 19 and the threaded end portion 20.

The effect of the decreasing diameter of the shank 18 of the pin is that upon rotation of the pin by means of the sleeve 11 engaging with the latching portion 13, the pin is free to swing to a limited extent about the latch. The tip of the threaded portion 20 thus describes a circle or some more complicated figure within a circular area as a result of the shank repeatedly engaging the lower end of the sleeve 11 and bounding off. This movement first facilitates finding of the hole into which the threaded portion is to be screwed and then allows alignment of the pin with the hole.

By way of example FIG. 2 shows part of one type of drive system for the sleeve 11. The sleeve is mounted in bearings 23 and 24 and has an external ring gear 25. The gear 25 is engaged by a ring gear 26 fixed to the end of a drive shaft 27 to which drive is transmitted from an electric motor in conventional manner.

I claim:

1. A dentine pin for fitting in a standard dental handpiece having a rotatable cylindrical sleeve, the pin comprising a shank with a latching portion at one end and a threaded portion attached to the other end of the shank by a neck in which the diameter of the shank decreases from a region adjacent the latching portion towards the neck and threaded portion in such a manner that the threaded portion can oscillate with respect to the axis of the sleeve of the handpiece, changing the inclination of the axis of the threaded portion to the axis of the sleeve, said shank being tapered and having a semi-cone angle of no more than 3°.

2. A dentine pin for fitting in a standard dental handpiece having a rotatable cylindrical sleeve, the pin comprising a shank with a latching portion at one end and a threaded portion attached to the other end of the shank by a neck in which the diameter of the shank decreases from a region adjacent the latching portion towards the neck and threaded portion in such a manner that the threaded portion can oscillate with respect to the axis of the sleeve of the handpiece, changing the inclination of the axis of the threaded portion to the axis of the sleeve, in which said neck is frusto-conical and tapers from a maximum diameter adjacent said shank to a minimum diameter adjacent said threaded portion, and including an annular groove formed at the junction between said shank and said frusto-conical neck to facilitate removal of said shank from said handpiece after said threaded portion has been broken off said neck.

3. In combination, a dentine pin releasably fitted in a standard dental handpiece for threading the pin into a pre-drilled hole in a tooth,
said handpiece having:
a latch; and
a rotatable cylindrical sleeve extending from said latch; and
said dentine pin having:
a locking portion at one end of the pin engageable with said latch in said dental handpiece;
a neck intermediate the ends of said pin; and
a shank extending from said locking portion through said sleeve in said handpiece and connecting to said neck;
a threaded portion defining the other end of said pin and threadable into said pre-drilled hole in a tooth; and
means floating the axis of said threaded portion with respect to the axis of said sleeve of said handpiece for self-alignment of said threaded portion with said pre-drilled hole in said tooth in automatic compensation for misalignment between the axes of said sleeve in said handpiece and said pre-drilled hole, said means comprising tapering of the portion of the shank within said cylindrical sleeve, in a direction from said locking portion toward said threaded portion with said threaded portion being fixed to the tapered end of said shank through said neck for limited sideways swinging of said threaded portion off the axis of said sleeve.

4. A dentine pin for fitting in a standard dental handpiece having a rotatable cylindrical sleeve, the pin having a shank with a latching portion at one end which comprises a part-annular groove for engagement by a latch of the dental handpiece and a flat for engagement with one end of the rotatable cylindrical sleeve of the handpiece, the pin having a threaded portion attached through a frangible portion to a neck connected to the other end of the shank, comprising the improvement in which the diameter of the shank decreases from the latching portion towards the threaded portion in such a manner that the shank can oscillate within and with respect to the axis of the sleeve of the handpiece, changing the inclination of the axis of the threaded portion to the axis of the sleeve, and including an annular groove formed at the junction between said shank and said neck to facilitate removal of said shank from said handpiece after said threaded portion has been broken off said neck.

* * * * *